United States Patent [19]
Hoskins et al.

[11] Patent Number: 5,834,270
[45] Date of Patent: Nov. 10, 1998

[54] BIOSYNTHETIC GENE MURD FROM *STREPTOCOCCUS PNEUMONIAE*

[75] Inventors: Jo Ann Hoskins, Indianapolis; Robert Brown Peery, Brownsburg; Paul Luther Skatrud; Chyun-Yeh Earnest Wu, both of Indianapolis, all of Ind.

[73] Assignee: Eli Lilly and Company, Indianapolis, Ind.

[21] Appl. No.: 843,309

[22] Filed: Apr. 14, 1997

Related U.S. Application Data

[62] Division of Ser. No. 665,435, Jun. 18, 1996, Pat. No. 5,681,694.

[51] Int. Cl.$^6$ ............................. C12N 15/00; C12N 9/00; C12N 5/00; C07H 21/04
[52] U.S. Cl. ..................... 435/172.3; 435/183; 435/243; 435/252.3; 435/320.1; 435/325; 536/23.2; 935/22
[58] Field of Search .................................. 435/172.3, 183, 435/243, 252.3, 320.1, 325; 536/23.2; 935/22

[56] References Cited

U.S. PATENT DOCUMENTS 5,681,694  10/1997  Hoskins et al. ............................. 435/4

OTHER PUBLICATIONS

Mengin–Lecreulx, et al., "Organization of the murE–murG Region Of *E. Coli*", *J. Bacteriol*, 171:11, pp. 6126–6134 (1989).

M. Ikeda, et al., "Homology Among murC, murD, murE and murF Proteins in *E. Coli* and Thet Between *E. Coli* murG And A Possible murG Protein in *B. Subtilis*", *J. Gen. Appl. Microbiol.*, 36, pp. 179–187 (1990).

Daniel, et al., "DNA sequence of the murE–murD region of *Bacillus subtilis* 168", *J. Gen. Microbiol.*, 139 (2); 361–370, (1993).

Leach et al., "*Rhizobium meliloti* homologs of *Escherichia coli* mur genes", *Gene*, 148, pp. 87–90, (1994).

Fleischmann et al., "Whole–genome random sequencing and assembly of *Haemophilus Influenzae* Rd", *Science*, 269, pp. 496–498 and 507–512, (1995).

*Primary Examiner*—Robert A. Wax
*Assistant Examiner*—Einar Stole
*Attorney, Agent, or Firm*—Thomas D. Webster; David E. Boone

[57] ABSTRACT

The invention provides isolated nucleic acid compounds encoding the murD stem peptide biosynthetic gene of *Streptococcus pneumoniae*. Also provided are vectors and transformed heterologous host cells for expressing the MurD enzyme product and a method for identifying compounds that inhibit stem peptide biosynthesis.

9 Claims, 1 Drawing Sheet

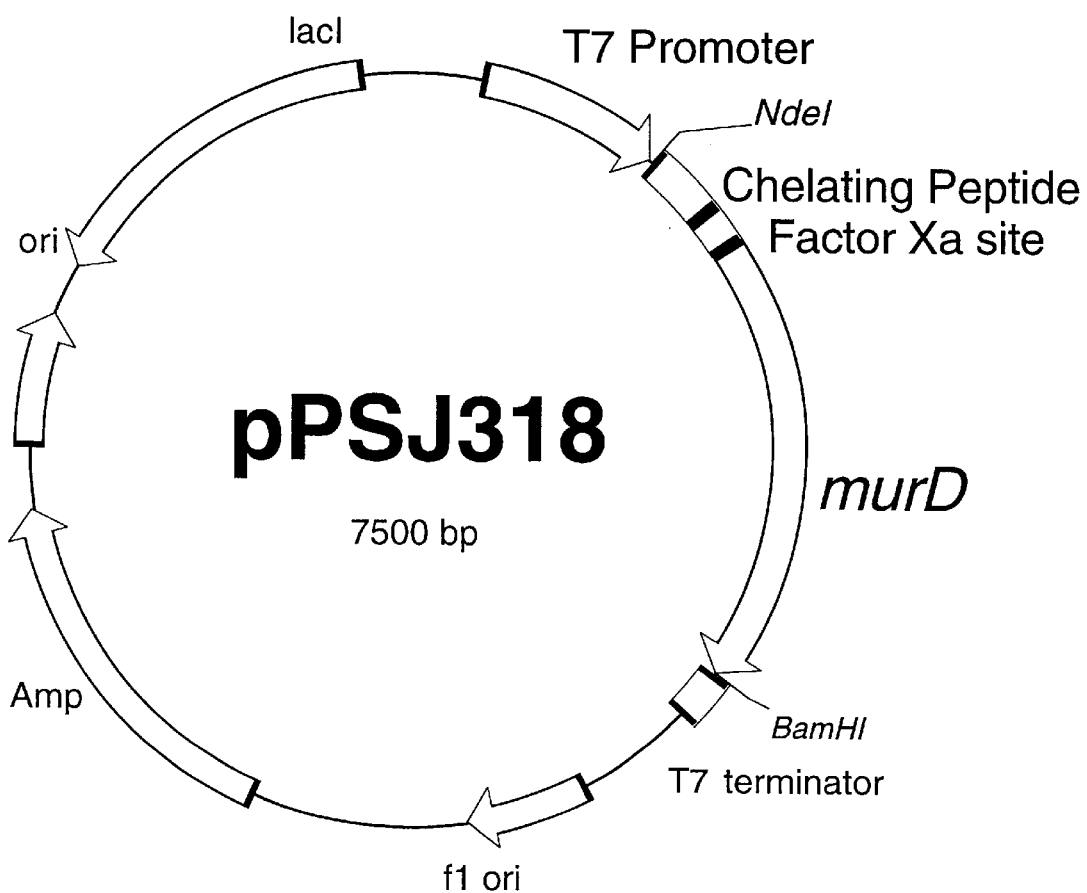

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1353 base pairs
        ( B ) TYPE: nucleic acid
        ( C ) STRANDEDNESS: single
        ( D ) TOPOLOGY: linear ( i i ) MOLECULE TYPE: DNA(genomic)

( i i i ) HYPOTHETICAL: NO ( i v ) ANTI-SENSE: NO ( i x ) FEATURE:
        ( A ) NAME/KEY: CDS
        ( B ) LOCATION: 1..1353

( x i ) SEQUENCE DESCRIPTION: SEQ ID NO:1:

```
ATG  AAA  GTA  ATA  GAT  CAA  TTT  AAA  AAT  AAG  AAA  GTT  CTT  GTT  TTA  GGT        48
Met  Lys  Val  Ile  Asp  Gln  Phe  Lys  Asn  Lys  Lys  Val  Leu  Val  Leu  Gly
  1                    5                   10                   15

TTG  GCC  AAG  TCT  GGT  GAA  TCT  GCA  GCT  CGT  TTG  TTG  GAC  AAG  CTA  GGT        96
Leu  Ala  Lys  Ser  Gly  Glu  Ser  Ala  Ala  Arg  Leu  Leu  Asp  Lys  Leu  Gly
         20                   25                   30

GCC  ATT  GTG  ACA  GTA  AAT  GAT  GGG  AAA  CCT  TTC  GAG  GAC  AAT  CCA  GCT       144
Ala  Ile  Val  Thr  Val  Asn  Asp  Gly  Lys  Pro  Phe  Glu  Asp  Asn  Pro  Ala
 35                   40                   45

GCC  CAA  AGT  TTG  CTG  GAA  GAA  GGG  ATC  AAG  GTC  ATT  ACA  GGT  GGC  CAT       192
Ala  Gln  Ser  Leu  Leu  Glu  Glu  Gly  Ile  Lys  Val  Ile  Thr  Gly  Gly  His
         50                   55                   60

CCT  TTG  GAA  CTC  TTG  GAT  GAA  GAG  TTT  GCC  CTT  ATG  GTG  AAA  AAT  CCA       240
Pro  Leu  Glu  Leu  Leu  Asp  Glu  Glu  Phe  Ala  Leu  Met  Val  Lys  Asn  Pro
 65                   70                   75                   80

GGT  ATC  CCC  TAC  AAC  AAT  CCC  ATG  ATT  GAA  AAG  GCT  TTG  GCC  AAG  AGA       288
Gly  Ile  Pro  Tyr  Asn  Asn  Pro  Met  Ile  Glu  Lys  Ala  Leu  Ala  Lys  Arg
 85                   90                   95

ATT  CCA  GTC  TTG  ACT  GAG  GTG  GAA  TTG  GCT  TAT  TTG  ATT  TCA  GAA  GCA       336
Ile  Pro  Val  Leu  Thr  Glu  Val  Glu  Leu  Ala  Tyr  Leu  Ile  Ser  Glu  Ala
        100                  105                  110

CCG  ATT  ATT  GGT  ATC  ACA  GGA  TCG  AAC  GGT  AAG  ACA  ACC  ACA  ACG  ACT       384
Pro  Ile  Ile  Gly  Ile  Thr  Gly  Ser  Asn  Gly  Lys  Thr  Thr  Thr  Thr  Thr
115                       120                  125

ATG  ATT  GGG  GAA  GTT  TTG  ACT  GCT  GCT  GGG  CAA  CAT  GGT  CTT  TTA  TCA       432
Met  Ile  Gly  Glu  Val  Leu  Thr  Ala  Ala  Gly  Gln  His  Gly  Leu  Leu  Ser
        130                  135                  140

GGG  AAT  ATC  GGC  TAT  CCT  GCC  AGT  CAG  GTT  GCT  CAA  ATA  GCA  TCA  GAT       480
Gly  Asn  Ile  Gly  Tyr  Pro  Ala  Ser  Gln  Val  Ala  Gln  Ile  Ala  Ser  Asp
145                       150                  155                  160
```

| | | | | | | | | | | | | | | | | |
|---|---|---|---|---|---|---|---|---|---|---|---|---|---|---|---|---|
| AAG | GAC | ACG | CTT | GTT | ATG | GAA | CTT | TCT | TCT | TTC | CAA | CTC | ATG | GGT | GTT | 528 |
| Lys | Asp | Thr | Leu | Val | Met | Glu | Leu | Ser | Ser | Phe | Gln | Leu | Met | Gly | Val | |
| 165 | | | | | 170 | | | | | 175 | | | | | | |
| CAA | GAA | TTC | CAT | CCA | GAG | ATT | GCG | GTT | ATT | ACC | AAC | CTC | ATG | CCA | ACT | 576 |
| Gln | Glu | Phe | His | Pro | Glu | Ile | Ala | Val | Ile | Thr | Asn | Leu | Met | Pro | Thr | |
| | 180 | | | | | 185 | | | | | 190 | | | | | |
| CAT | ATC | GAC | TAC | CAT | GGG | TCA | TTT | TCT | GAA | TAT | GTA | GCA | GCC | AAG | TGG | 624 |
| His | Ile | Asp | Tyr | His | Gly | Ser | Phe | Ser | Glu | Tyr | Val | Ala | Ala | Lys | Trp | |
| 195 | | | | | 200 | | | | | 205 | | | | | | |
| AAT | ATC | CAG | AAC | AAG | ATG | ACA | GCA | GCT | GAT | TTC | CTT | GTC | TTG | AAC | TTT | 672 |
| Asn | Ile | Gln | Asn | Lys | Met | Thr | Ala | Ala | Asp | Phe | Leu | Val | Leu | Asn | Phe | |
| | 210 | | | | | 215 | | | | | 220 | | | | | |
| AAT | CAA | GAC | TTG | GCA | AAA | GAC | TTG | ACT | TCC | AAG | ACA | GAA | GCC | ACT | GTT | 720 |
| Asn | Gln | Asp | Leu | Ala | Lys | Asp | Leu | Thr | Ser | Lys | Thr | Glu | Ala | Thr | Val | |
| 225 | | | | | 230 | | | | | 235 | | | | | 240 | |
| GTA | CCA | TTT | TCA | ACA | CTT | GAA | AAG | GTT | GAT | GGA | GCT | TAT | CTG | GAA | GAT | 768 |
| Val | Pro | Phe | Ser | Thr | Leu | Glu | Lys | Val | Asp | Gly | Ala | Tyr | Leu | Glu | Asp | |
| 245 | | | | | 250 | | | | | 255 | | | | | | |
| GGT | CAA | CTC | TAC | TTC | CGT | GGT | GAA | GTA | GTC | ATG | GCA | GCG | AAT | GAA | ATC | 816 |
| Gly | Gln | Leu | Tyr | Phe | Arg | Gly | Glu | Val | Val | Met | Ala | Ala | Asn | Glu | Ile | |
| | 260 | | | | | 265 | | | | | 270 | | | | | |
| GGT | GTT | CCA | GGT | AGC | CAC | AAT | GTG | GAA | AAT | GCC | CTT | GCG | ACT | ATT | GCT | 864 |
| Gly | Val | Pro | Gly | Ser | His | Asn | Val | Glu | Asn | Ala | Leu | Ala | Thr | Ile | Ala | |
| 275 | | | | | 280 | | | | | 285 | | | | | | |
| GTA | GCC | AAG | CTT | CGT | GAT | GTG | GAC | AAT | CAA | ACC | ATC | AAG | GAA | ACT | CTT | 912 |
| Val | Ala | Lys | Leu | Arg | Asp | Val | Asp | Asn | Gln | Thr | Ile | Lys | Glu | Thr | Leu | |
| | 290 | | | | | 295 | | | | | 300 | | | | | |
| TCA | GCC | TTC | GGT | GGT | GTC | AAA | CAC | CGT | CTC | CAG | TTT | GTG | GAT | GAC | ATC | 960 |
| Ser | Ala | Phe | Gly | Gly | Val | Lys | His | Arg | Leu | Gln | Phe | Val | Asp | Asp | Ile | |
| 305 | | | | | 310 | | | | | 315 | | | | | 320 | |
| AAG | GGT | GTT | AAA | TTC | TAT | AAC | GAC | AGT | AAA | TCA | ACT | AAT | ATC | TTG | GCT | 1008 |
| Lys | Gly | Val | Lys | Phe | Tyr | Asn | Asp | Ser | Lys | Ser | Thr | Asn | Ile | Leu | Ala | |
| 325 | | | | | 330 | | | | | 335 | | | | | | |
| ACT | CAA | AAA | GCC | TTA | TCA | GGA | TTT | GAC | AAC | AGC | AAG | GTC | GTC | TTG | ATT | 1056 |
| Thr | Gln | Lys | Ala | Leu | Ser | Gly | Phe | Asp | Asn | Ser | Lys | Val | Val | Leu | Ile | |
| | 340 | | | | | 345 | | | | | 350 | | | | | |
| GCA | GGT | GGT | TTG | GAC | CGT | GGC | AAT | GAG | TTT | GAC | GAA | TTG | GTG | CCA | GAC | 1104 |
| Ala | Gly | Gly | Leu | Asp | Arg | Gly | Asn | Glu | Phe | Asp | Glu | Leu | Val | Pro | Asp | |
| 355 | | | | | 360 | | | | | 365 | | | | | | |
| ATT | ACT | GGA | CTC | AAG | AAG | ATG | GTC | ATC | CTG | GGT | CAA | TCT | GCA | GAA | CGT | 1152 |
| Ile | Thr | Gly | Leu | Lys | Lys | Met | Val | Ile | Leu | Gly | Gln | Ser | Ala | Glu | Arg | |
| | 370 | | | | | 375 | | | | | 380 | | | | | |
| GTC | AAA | CGG | GCA | GCA | GAC | AAG | GCT | GGT | GTC | GCT | TAT | GTG | GAG | GCG | ACA | 1200 |
| Val | Lys | Arg | Ala | Ala | Asp | Lys | Ala | Gly | Val | Ala | Tyr | Val | Glu | Ala | Thr | |
| 385 | | | | | 390 | | | | | 395 | | | | | 400 | |
| GAT | ATT | GCA | GAT | GCG | ACC | CGC | AAG | GCC | TAT | GAG | CTT | GCG | ACT | CAA | GGA | 1248 |
| Asp | Ile | Ala | Asp | Ala | Thr | Arg | Lys | Ala | Tyr | Glu | Leu | Ala | Thr | Gln | Gly | |
| 405 | | | | | 410 | | | | | 415 | | | | | | |
| GAT | GTG | GTT | CTT | CTT | AGT | CCT | GCC | AAT | GCC | AGC | TGG | GAT | ATG | TAT | GCT | 1296 |
| Asp | Val | Val | Leu | Leu | Ser | Pro | Ala | Asn | Ala | Ser | Trp | Asp | Met | Tyr | Ala | |
| | 420 | | | | | 425 | | | | | 430 | | | | | |
| AAC | TTT | GAA | GTA | CGT | GGC | GAC | CTC | TTT | ATC | GAC | ACA | GTA | GCG | GAG | TTA | 1344 |
| Asn | Phe | Glu | Val | Arg | Gly | Asp | Leu | Phe | Ile | Asp | Thr | Val | Ala | Glu | Leu | |
| 435 | | | | | 440 | | | | | 445 | | | | | | |
| AAA | GAA | TAA | | | | | | | | | | | | | | 1353 |
| Lys | Glu | | | | | | | | | | | | | | | |
| 450 | | | | | | | | | | | | | | | | |

( 2 ) INFORMATION FOR SEQ ID NO:2:

( i ) SEQUENCE CHARACTERISTICS:
   ( A ) LENGTH: 450 amino acids
   ( B ) TYPE: amino acid
   ( D ) TOPOLOGY: linear ( i i ) MOLECULE TYPE: protein ( x i ) SEQUENCE DESCRIPTION: SEQ ID NO:2:

```
Met Lys Val Ile Asp Gln Phe Lys Asn Lys Val Leu Val Leu Gly
 1               5                  10                  15

Leu Ala Lys Ser Gly Glu Ser Ala Ala Arg Leu Leu Asp Lys Leu Gly
         20                  25                  30

Ala Ile Val Thr Val Asn Asp Gly Lys Pro Phe Glu Asp Asn Pro Ala
 35                      40                  45

Ala Gln Ser Leu Leu Glu Glu Gly Ile Lys Val Ile Thr Gly Gly His
         50                  55                  60

Pro Leu Glu Leu Leu Asp Glu Glu Phe Ala Leu Met Val Lys Asn Pro
 65                      70                  75                  80

Gly Ile Pro Tyr Asn Asn Pro Met Ile Glu Lys Ala Leu Ala Lys Arg
 85                      90                  95

Ile Pro Val Leu Thr Glu Val Glu Leu Ala Tyr Leu Ile Ser Glu Ala
     100                 105                 110

Pro Ile Ile Gly Ile Thr Gly Ser Asn Gly Lys Thr Thr Thr Thr Thr
 115                     120                 125

Met Ile Gly Glu Val Leu Thr Ala Ala Gly Gln His Gly Leu Leu Ser
     130                 135                 140

Gly Asn Ile Gly Tyr Pro Ala Ser Gln Val Ala Gln Ile Ala Ser Asp
 145                     150                 155                 160

Lys Asp Thr Leu Val Met Glu Leu Ser Ser Phe Gln Leu Met Gly Val
 165                     170                 175

Gln Glu Phe His Pro Glu Ile Ala Val Ile Thr Asn Leu Met Pro Thr
     180                 185                 190

His Ile Asp Tyr His Gly Ser Phe Ser Glu Tyr Val Ala Ala Lys Trp
 195                     200                 205

Asn Ile Gln Asn Lys Met Thr Ala Ala Asp Phe Leu Val Leu Asn Phe
     210                 215                 220

Asn Gln Asp Leu Ala Lys Asp Leu Thr Ser Lys Thr Glu Ala Thr Val
 225                     230                 235                 240

Val Pro Phe Ser Thr Leu Glu Lys Val Asp Gly Ala Tyr Leu Glu Asp
 245                     250                 255

Gly Gln Leu Tyr Phe Arg Gly Glu Val Val Met Ala Ala Asn Glu Ile
     260                 265                 270

Gly Val Pro Gly Ser His Asn Val Glu Asn Ala Leu Ala Thr Ile Ala
 275                     280                 285

Val Ala Lys Leu Arg Asp Val Asp Asn Gln Thr Ile Lys Glu Thr Leu
     290                 295                 300

Ser Ala Phe Gly Gly Val Lys His Arg Leu Gln Phe Val Asp Asp Ile
 305                     310                 315                 320

Lys Gly Val Lys Phe Tyr Asn Asp Ser Lys Ser Thr Asn Ile Leu Ala
 325                     330                 335

Thr Gln Lys Ala Leu Ser Gly Phe Asp Asn Ser Lys Val Val Leu Ile
     340                 345                 350

Ala Gly Gly Leu Asp Arg Gly Asn Glu Phe Asp Glu Leu Val Pro Asp
 355                     360                 365

Ile Thr Gly Leu Lys Lys Met Val Ile Leu Gly Gln Ser Ala Glu Arg
     370                 375                 380
```

| | | | | | | | | | | | | | |
|---|---|---|---|---|---|---|---|---|---|---|---|---|---|
| Val | Lys | Arg | Ala | Ala | Asp | Lys | Ala | Gly | Val | Ala | Tyr | Val | Glu | Ala | Thr |
| 385 | | | | | 390 | | | | | 395 | | | | | 400 |

| Asp | Ile | Ala | Asp | Ala | Thr | Arg | Lys | Ala | Tyr | Glu | Leu | Ala | Thr | Gln | Gly |
|---|---|---|---|---|---|---|---|---|---|---|---|---|---|---|---|
| 405 | | | | | 410 | | | | | 415 | | | | | |

| Asp | Val | Val | Leu | Leu | Ser | Pro | Ala | Asn | Ala | Ser | Trp | Asp | Met | Tyr | Ala |
|---|---|---|---|---|---|---|---|---|---|---|---|---|---|---|---|
| | 420 | | | | | 425 | | | | | 430 | | | | |

| Asn | Phe | Glu | Val | Arg | Gly | Asp | Leu | Phe | Ile | Asp | Thr | Val | Ala | Glu | Leu |
|---|---|---|---|---|---|---|---|---|---|---|---|---|---|---|---|
| 435 | | | | | 440 | | | | | 445 | | | | | |

Lys Glu
 450

( 2 ) INFORMATION FOR SEQ ID NO:3:

( i ) SEQUENCE CHARACTERISTICS:
        ( A ) LENGTH: 1350 base pairs
        ( B ) TYPE: nucleic acid
        ( C ) STRANDEDNESS: single
        ( D ) TOPOLOGY: linear ( i i ) MOLECULE TYPE: mRNA ( i i i ) HYPOTHETICAL: NO ( i v ) ANTI-SENSE: NO ( x i ) SEQUENCE DESCRIPTION: SEQ ID NO:3:

| | | | | | | |
|---|---|---|---|---|---|---|
| AUGAAAGUAA | UAGAUCAAUU | UAAAAAUAAG | AAAGUUCUUG | UUUUAGGUUU | GGCCAAGUCU | 60 |
| GGUGAAUCUG | CAGCUCGUUU | GUUGGACAAG | CUAGGUGCCA | UUGUGACAGU | AAAUGAUGGG | 120 |
| AAACCUUUCG | AGGACAAUCC | AGCUGCCCAA | AGUUUGCUGG | AAGAAGGGAU | CAAGGUCAUU | 180 |
| ACAGGUGGCC | AUCCUUUGGA | ACUCUUGGAU | GAAGAGUUUG | CCCUUAUGGU | GAAAAAUCCA | 240 |
| GGUAUCCCCU | ACAACAAUCC | CAUGAUUGAA | AAGGCUUUGG | CCAAGAGAAU | UCCAGUCUUG | 300 |
| ACUGAGGUGG | AAUUGGCUUA | UUUGAUUUCA | GAAGCACCGA | UUAUGGUAU | CACAGGAUCG | 360 |
| AACGGUAAGA | CAACCACAAC | GACUAUGAUU | GGGAAGUUU | UGACUGCUGC | UGGGCAACAU | 420 |
| GGUCUUUUAU | CAGGGAAUAU | CGGCUAUCCU | GCCAGUCAGG | UUGCUCAAAU | AGCAUCAGAU | 480 |
| AAGGACACGC | UUGUUAUGGA | ACUUUCUUCU | UUCCAACUCA | UGGGUGUUCA | AGAAUUCCAU | 540 |
| CCAGAGAUUG | CGGUUAUUAC | CAACCUCAUG | CCAACUCAUA | UCGACUACCA | UGGGUCAUUU | 600 |
| UCUGAAUAUG | UAGCAGCCAA | GUGGAAUAUC | CAGAACAAGA | UGACAGCAGC | UGAUUUCCUU | 660 |
| GUCUUGAACU | UUAAUCAAGA | CUUGGCAAAA | GACUUGACUU | CCAAGACAGA | AGCCACUGUU | 720 |
| GUACCAUUUU | CAACACUUGA | AAAGGUUGAU | GGAGCUUAUC | UGGAAGAUGG | UCAACUCUAC | 780 |
| UUCCGUGGUG | AAGUAGUCAU | GGCAGCGAAU | GAAAUCGGUG | UUCCAGGUAG | CCACAAUGUG | 840 |
| GAAAAUGCCC | UUGCGACUAU | UGCUGUAGCC | AAGCUUCGUG | AUGUGGACAA | UCAAACCAUC | 900 |
| AAGGAAACUC | UUUCAGCCUU | CGGUGGUGUC | AAACACCGUC | UCCAGUUUGU | GGAUGACAUC | 960 |
| AAGGGUGUUA | AAUUCUAUAA | CGACAGUAAA | UCAACUAAUA | UCUUGGCUAC | UCAAAAAGCC | 1020 |
| UUAUCAGGAU | UUGACAACAG | CAAGGUCGUC | UUGAUUGCAG | GUGGUUUGGA | CCGUGGCAAU | 1080 |
| GAGUUUGACG | AAUUGGUGCC | AGACAUUACU | GGACUCAAGA | AGAUGGUCAU | CCUGGGUCAA | 1140 |
| UCUGCAGAAC | GUGUCAAACG | GGCAGCAGAC | AAGGCUGGUG | UCGCUUAUGU | GGAGGCGACA | 1200 |
| GAUAUUGCAG | AUGCGACCCG | CAAGGCCUAU | GAGCUUGCGA | CUCAAGGAGA | UGUGGUUCUU | 1260 |
| CUUAGUCCUG | CCAAUGCCAG | CUGGGAUAUG | UAUGCUAACU | UGAAGUACG | UGGCGACCUC | 1320 |
| UUUAUCGACA | CAGUAGCGGA | GUUAAAAGAA | | | | 1350 |

BIOSYNTHETIC GENE MURD FROM *STREPTOCOCCUS PNEUMONIAE*

This application is a division of application Ser. No. Ser. No. 08/665,435 filed on Jun. 18, 1996, now U.S. Pat. No. 5,681,694.

BACKGROUND OF THE INVENTION

This invention relates to recombinant DNA technology. In particular the invention pertains to the cloning of the murD gene encoding uridine-diphosphate-N-acetylmuramyl-L-alanyl-D-isoglutamate ligase of *Streptococcus pneumoniae* and the use of the murD gene and the encoded protein in a screen for new inhibitors of bacterial cell wall biosynthesis.

The emergence of antibiotic resistance in common pathogenic bacterial species has justifiably alarmed the medical and research communities. Frequently these organisms are co-resistant to several different antibacterial agents. Pathogens resistant to frequently utilized antibiotics are found in the clinical as well as the community setting. Particularly problematic in the community setting has been the emergence and rapid spread of beta-lactam resistance in *Streptococcus pneumoniae* which frequently causes upper respiratory tract infections. Resistance to beta-lactams in this organism is due to modification of one or more of the penicillin-binding proteins (PBP's) which are involved in cell wall biosynthesis and are the targets for beta-lactam antibiotics.

Interference with bacterial cell wall biosynthesis is an especially attractive antibacterial target because an analogous structure does not exist in mammalian cells so that compounds that interfere with cell wall biosynthesis have low toxicity in humans and potentially high therapeutic value.

The bacterial cell wall structure contains a peptidoglycan layer which provides mechanical rigidity for the bacterium. This segment of the cell wall is composed of a sugar backbone (alternating residues of N-acetylglucosamine and N-acetylmuramic acid) attached to a pentapeptide (also referred to as "stem peptide," or "Park nucleotide") containing alternating D and L amino acid residues. The nascent peptidoglycan layer is stabilized by an enzymatic step which crosslinks adjacent pentapeptide moieties. Without this crosslinking step the peptidoglycan structure is severely weakened and susceptible to degradation. Indeed, it is this crosslinking step that has been a frequently targeted site for antibiotic compounds such as the beta-lactam antibiotics.

In contrast to the beta-lactam case, which targets the crosslinking step, the pathway involved in the synthesis of the stem peptide has not been widely exploited as a target for inhibitory compounds. The stem peptide biosynthetic pathway comprises at least 10 steps in which the stem peptide is added onto UDPMurNAc by the stepwise addition of amino acid residues. In the first step, catalyzed by the UDPGlcNAc enolpyruvyl transferase and NADH-dependent reductase, UDPGlcNAc is converted to UDPMurNAc. In five subsequent steps, catalyzed by UDP-N-acetylmuramate:L-alanine ligase; UDP-N-acetyl-muramyl-L-alanine:D-glutamate ligase; UDP-N-acetyl-muramyl-L-alanyl-D-isoglutamate:L-lysine ligase; UDP-N-acetylmuramyl-L-alanyl-D-isoglutamyl-L-lysine:D-alanyl-D-alanine ligase; and D-alanyl-D-alanine synthetase, the final product, UDPMurNAc-L-Ala-D-isoGlu-L-lysine-D-Ala-D-Ala, is produced in *Streptococcus pneumoniae*.

The enzymatic steps involved in the formation of the stem peptide are potentially a rich source for new antibacterial targets. A few inhibitors, which target this pathway, have been developed. For example, D-cycloserine inhibits alanine racemase and D-alanine-D-alanine synthetase; phosphonomycin inhibits the conversion of UDP-GlcNAc to UDP-GlcNac-enolpyruvate; and Ala-phosphonine inhibits the formation of UDP-MurNac-L-Ala.

The genes directly involved with assembly of the stem peptide in *Escherichia coli* have been cloned and characterized. These genes occur in two clusters on the *E. coli* chromosome. Analogous genes have been cloned from *Bacillus subtilus,* and from *Haemophilus influenzae* (Fleischmann et al., Science, 269:496–512 (1996)).

While inroads in the development of new antibiotics and new targets for antibiotic compounds have been made with a variety of microorganisms, progress has been less apparent in *Streptococcus pneumoniae*. In part, *Streptococcus pneumoniae* presents a special case because the organism is highly mutagenic and readily takes up exogenous DNA from its surroundings. Thus, the need for new antibacterial compounds and new targets for antibacterial therapy is especially acute in *Streptococcus pneumoniae*.

SUMMARY OF THE INVENTION

The present invention is designed to meet the aforementioned need and provides, inter alia, isolated nucleic acid molecules that encode the murD gene product from *Streptococcus pneumoniae*. The invention also provides the protein product of the *Streptococcus pneumoniae* murD gene, uridine-diphosphate-N-acetylmuramyl-L-alanyl-D-isoglutamate ligase (MurD protein), in substantially purified form.

Having the cloned murD gene of *Streptococcus pneumoniae* enables the production of recombinant MurD protein and the implementation of large scale screens to identify new antibacterial compounds targeted at the stem peptide biosynthetic pathway. It may be possible to combine stem peptide proteins in a single screen to examine several steps at the same time. Structural analysis of the MurD protein will enable structure-based drug design to develop novel compounds effective in the treatment of antibiotic resistant microorganisms.

In one embodiment the present invention relates to an isolated DNA molecule encoding MurD protein, said DNA molecule comprising the nucleotide sequence identified as SEQ ID NO. 1:

```
ATG AAA GTA ATA GAT CAA TTT AAA

AAT AAG AAA GTT CTT GTT TTA GGT      48

TTG GCC AAG TCT GGT GAA TCT GCA

GCT CGT TTG TTG GAC AAG CTA GGT      96

GCC ATT GTG ACA GTA AAT GAT GGG

AAA CCT TTC GAG GAC AAT CCA GCT     144

GCC CAA AGT TTG CGT GAA GAA GGG

ATC AAG GTC ATT ACA GGT GGC CAT     192
```

```
                         -continued                                        -continued
CCT TTG GAA CTC TTG GAT GAA GAG                       GTA GCC AAG CTT CGT GAT GTG GAC TTT GCC CTT ATG GTG AAA AAT CCA    240                AAT CAA ACC ATC AAG GAA ACT CTT    912

GGT ATC CCC TAC AAC AAT CCC ATG                       TCA GCC TTC GGT GGT GTC AAA CAC

ATT GAA AAG GCT TTG GCC AAG AGA    288                CGT CTC CAG TTT GTG GAT GAC ATC    960

ATT CCA GTC TTG ACT GAG GTG GAA                       AAG GGT GTT AAA TTC TAT AAC GAC

TTG GCT TAT TTG ATT TCA GAA GCA    336                AGT AAA TCA ACT AAT ATC TTG GCT   1008

CCG ATT ATT GGT ATC ACA GGA TCG                       ACT CAA AAA GCC TTA TCA GGA TTT

AAC GGT AAG ACA ACC ACA ACG ACT    384                GAC AAC AGC AAG GTC GTC TTG ATT   1056

ATG ATT GGG GAA GTT TTG ACT GCT                       GCA GGT GGT TTG GAC CGT GGC AAT

GCT GGG CAA CAT GGT CTT TTA TCA    432                GAG TTT GAC GAA TTG GTG CCA GAC   1104

GGG AAT ATC GGC TAT CCT GCC AGT                       ATT ACT GGA CTC AAG AAG ATG GTC

CAG GTT GCT CAA ATA GCA TCA GAT    480                ATC CTG GGT CAA TCT GCA GAA CGT   1152

AAG GAC ACG CTT GTT ATG GAA CTT                       GTC AAA CGG GCA GCA GAC AAG GCT

TCT TCT TTC CAA CTC ATG GGT GTT    528                GGT GTC GCT TAT GTG GAG GCG ACA   1200

CAA GAA TTC CAT CCA GAG ATT GCG                       GAT ATT GCA GAT GCG ACC CGC AAG

GTT ATT ACC AAC CTC ATG CCA ACT    576                GCC TAT GAG CTT GCG ACT CAA GGA   1248

CAT ATC GAC TAC CAT GGG TCA TTT                       GAT GTG GTT CTT CTT AGT CCT GCC

TCT GAA TAT GTA GCA GCC AAG TGG    624                AAT GCC AGC TGG GAT ATG TAT GCT   1296

AAT ATC CAG AAC AAG ATG ACA GCA                       AAC TTT GAA GTA CGT GGC GAC CTC

GCT GAT TTC CTT GTC TTG AAC TTT    672                TTT ATC GAC ACA GTA GCG GAG TTA   1344

AAT CAA GAC TTG GCA AAA GAC TTG                       AAA GAA                                  1350

ACT TCC AAG ACA GAA GCC ACT GTT    720
```

In another embodiment the present invention relates to a MurD protein molecule, encoded by SEQ ID NO:1 wherein said MurD protein molecule comprises the sequence identified as SEQ ID NO. 2.

```
GTA CCA TTT TCA ACA CTT GAA AAG
```

In a further embodiment the present invention relates to a ribonucleic acid molecule encoding MurD protein, said ribonucleic acid molecule comprising the sequence identified as SEQ ID NO. 3:

```
        GTT GAT GGA GCT TAT CTG GAA GAT    768
```

In yet another embodiment, the present invention relates to a recombinant DNA vector which incorporates the *Streptococcus pneumoniae* murD gene in operable linkage to gene expression sequences enabling the murD gene to be transcribed and translated in a host cell.

```
GGT CAA CTC TAC TTC CGT GGT GAA

GTA GTC ATG GCA GCG AAT GAA ATC    816

GGT GTT CCA GGT AGC CAC AAT GTG
```

In still another embodiment the present invention relates to homologous or heterologous host cells which have been transformed or transfected with the cloned murD gene of *Streptococcus pneumoniae* such that the murD gene is expressed in the host cell.

```
        GAA AAT GCC CTT GCG ACT ATT GCT    864
```

In a still further embodiment, the present invention relates to a method for identifying compounds that inhibit the enzymatic activity of the MurD protein of *Streptococcus pneumoniae*.

DESCRIPTION OF THE DRAWING

FIGURE. Plasmid pPSJ318, which is useful for high level expression of the *Streptococcus pneumoniae* murD gene in heterologous or homologous procaryotic host cells.

DEFINITIONS

The terms "cleavage" or "restriction" of DNA refers to the catalytic cleavage of the DNA with a restriction enzyme that acts only at certain sequences in the DNA (viz. sequence-specific endonucleases). The various restriction enzymes used herein are commercially available and their reaction conditions, cofactors, and other requirements are used in the manner well known to one of ordinary skill in the art. Appropriate buffers and substrate amounts for particular restriction enzymes are specified by the manufacturer or can readily be found in the literature.

The term "fusion protein" denotes a hybrid protein molecule not found in nature comprising a translational fusion or enzymatic fusion in which two or more different proteins or fragments thereof are covalently linked on a single polypeptide chain.

The term "plasmid" refers to an extrachromosomal genetic element. The starting plasmids herein are either commercially available, publicly available on an unrestricted basis, or can be constructed from available plasmids in accordance with published procedures. In addition, equivalent plasmids to those described are known in the art and will be apparent to the ordinarily skilled artisan.

"Recombinant DNA cloning vector" as used herein refers to any autonomously replicating agent, including, but not limited to, plasmids and phages, comprising a DNA molecule to which one or more additional DNA segments can or have been added.

The term "recombinant DNA expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The terms "complementary" or "complementarity" as used herein refers to the capacity of purine and pyrimidine nucleotides to associate through hydrogen bonding in double stranded nucleic acid molecules. The following base pairs are complementary: guanine and cytosine; adenine and thymine; and adenine and uracil.

"Isolated nucleic acid compound" refers to any RNA or DNA sequence, however constructed or synthesized, which is locationally distinct from its natural location.

A "primer" is a nucleic acid fragment which functions as an initiating substrate for enzymatic or synthetic elongation of, for example, a nucleic acid molecule.

The term "promoter" refers to a DNA sequence which directs transcription of DNA to RNA.

A "probe" as used herein is a labeled nucleic acid compound which hybridizes with another nucleic acid compound.

The term "hybridization" as used herein refers to a process in which a strand of nucleic acid joins with a complementary strand through base pairing. "Selective hybridization" refers to hybridization that occurs under conditions of high stringency. The degree of hybridization between nucleic acid molecules varies with the degree of complementarity, the stringency of the hybridization conditions, and with the length of the strands.

The term "stringency" refers to a set of hybridization conditions, for example temperature and salt concentration, which may be varied to achieve "high stringency" or "low stringency" conditions, thereby varying the degree of hybridization of one nucleic acid molecule with another nucleic acid molecule. High stringency conditions disfavor non-homologous basepairing.

DETAILED DESCRIPTION

The murD gene of *Streptococcus pneumoniae* encodes an enzyme involved in stem peptide biosynthesis. The stem peptide pathway is necessary for the synthesis of the peptidoglycan layer which is part of the bacterial cell wall. There are at least 10 steps involved in stem peptide biosynthesis. The murD gene encodes uridine-diphosphate-N-acetylmuramyl-L-alanyl-D-isoglutamate ligase (SEQ ID NO. 2), which catalyzes the addition of D-Glu to UDPMurNAc-L-Ala forming UDPMurNAc-L-Ala-D-isoGlu.

The murD gene of *Streptococcus pneumoniae* comprises a DNA sequence of 1350 nucleotide base pairs (SEQ ID NO. 1). There are no intervening sequences. Those skilled in the art will recognize that owing to the degeneracy of the genetic code (i.e. 64 codons which encode 20 amino acids), numerous "silent" substitutions of nucleotide base pairs could be introduced into the sequence identified as SEQ ID NO. 1 without altering the identity of the encoded amino acid(s) or protein product. All such substitutions are intended to be within the scope of the invention.

Gene Isolation Procedures

Those skilled in the art will recogize that the murD gene may be obtained by a plurality of applicable genetic and recombinant DNA techniques including, for example, polymerase chain reaction (PCR) amplification, or de novo DNA synthesis. (See e.g., J. Sambrook et al. *Molecular Cloning*, 2d Ed. Chap. 14 (1989)).

Methods for constructing gene libraries in a suitable vector such as a plasmid or phage for propagation in procaryotic or eucaryotic cells are well known to those skilled in the art. [See e.g. J. Sambrook et al. Supra]. Suitable cloning vectors are widely available.

Skilled artisans will recognize that the murD gene of *Streptococcus pneumoniae* or fragment thereof could also be isolated by PCR amplification of *Streptococcus pneumoniae* genomic DNA using oligonucleotide primers targeted to any suitable region of SEQ ID NO. 1. Methods for PCR amplification are widely known in the art. See e.g. *PCR Protocols: A Guide to Method and Application*, Ed. M. Innis et al., Academic Press (1990). The amplification reaction comprises genomic DNA, suitable enzymes, primers, and buffers, and is conveniently carried out in a DNA Thermal Cycler (Perkin Elmer Cetus, Norwalk, Conn.). A positive result is determined by detecting an appropriately-sized DNA fragment following agarose gel electrophoresis.

Protein Production Methods

One of the embodiments of the present invention is the purified protein encoded by the murD gene or functionally related proteins of *Streptococcus pneumoniae*.

Skilled artisans will recognize that the proteins of the present invention can be synthesized by any number of different methods. The amino acid compounds of the invention can be made by chemical methods well known in the art, including solid phase peptide synthesis or recombinant methods. Both methods are described in U.S. Pat. No. 4,617,149, incorporated herein by reference.

The principles of solid phase chemical synthesis of polypeptides are well known in the art and may be found in general texts in the area. See, e.g., H. Dugas and C. Penney, *Bioorganic Chemistry* (1981) Springer-Verlag, New York, 54–92. For example, peptides may be synthesized by solid-phase methodology utilizing an Applied Biosystems 430A peptide synthesizer (Applied Biosystems, Foster City, Calif.) and synthesis cycles supplied by Applied Biosystems. Protected amino acids, such as t-butoxycarbonyl-protected amino acids, and other reagents are commercially available from many chemical supply houses.

Sequential t-butoxycarbonyl chemistry using double-couple protocols are applied to the starting p-methyl benzhydryl amine resins for the production of C-terminal carboxamides. For the production of C-terminal acids, the corresponding pyridine-2-aldoxime methiodide resin is used. Asparagine, glutamine, and arginine are coupled using preformed hydroxy benzotriazole esters. Following completion of the synthesis the peptides may be deprotected and cleaved from the resin with anhydrous hydrogen fluoride containing 10% meta-cresol. Cleavage of the side chain protecting group(s) and of the peptide from the resin is carried out at zero degrees Celcius or below, preferably –20° C. for thirty minutes followed by thirty minutes at 0° C.

The protein of the present invention can also be produced by recombinant DNA methods using the cloned murD gene of *Streptococcus pneumoniae*. Recombinant methods are preferred if a high yield is desired. Expression of the cloned murD gene can be carried out in a variety of suitable host cells well known to those skilled in the art. The murD gene is introduced into a host cell by any suitable means, well known to those skilled in the art. While chromosomal integration of the cloned murD gene is within the scope of the present invention, it is preferred that the gene be cloned into a suitable extra-chromosomally maintained expression vector so that the coding region of the murD gene is operably linked to a constitutive or inducible promoter.

The basic steps in the recombinant production of the MurD protein are:

a) constructing a natural, synthetic or semi-synthetic DNA encoding MurD protein;

b) integrating said DNA into an expression vector in a manner suitable for expressing the MurD protein, either alone or as a fusion protein;

c) transforming an appropriate eucaryotic or prokaryotic host cell with said expression vector, d) culturing said transformed host cell in a manner to express the MurD protein; and e) recovering and purifying the MurD protein by any suitable means, well known to those skilled in the art.

Expressing Recombinant MurD Protein in Procaryotic and Eucaryotic Host Cells

In general, prokaryotes are used for cloning DNA sequences and for constructing the vectors of the present invention. Prokaryotes are also employed in the production of the MurD protein. For example, the *Escherichia coli* K12 strain 294 (ATCC No. 31446) is particularly useful for the prokaryotic expression of foreign proteins. Other strains of *E. coli*, bacilli such as *Bacillus subtilis,* enterobacteriaceae such as *Salmonella typhimurium* or *Serratia marcescans,* various Pseudomonas species and other bacteria, such as Streptomyces, may also be employed as host cells in the cloning and expression of the recombinant proteins of this invention.

Promoters suitable for driving the expression of gene sequences in prokaryotes include βlactamase [e.g. vector pGX2907, ATCC 39344, contains a replicon and -β lactamase gene], lactose systems [Chang et al., Nature (London), 275:615 (1978); Goeddel et al., Nature (London), 281:544 (1979)], alkaline phosphatase, and the tryptophan (trp) promoter system [vector pATH1 (ATCC 37695) which is designed to facilitate expression of an open reading frame as a trpE fusion protein under the control of the trp promoter]. Hybrid promoters such as the tac promoter (isolatable from plasmid pDR540, ATCC-37282) are also suitable. Still other bacterial promoters, whose nucleotide sequences are generally known, enable one of skill in the art to ligate such promoter sequences to DNA encoding the proteins of the instant invention using linkers or adapters to supply any required restriction sites. Promoters for use in bacterial systems also will contain a Shine-Dalgarno sequence operably linked to the DNA encoding the desired polypeptides. These examples are illustrative rather than limiting.

The protein of this invention may be synthesized either by direct expression or as a fusion protein comprising the protein of interest as a translational fusion with another protein or peptide which may be removable by enzymatic or chemical cleavage. It is often observed in the production of certain peptides in recombinant systems that expression as a fusion protein prolongs the lifespan, increases the yield of the desired peptide, or provides a convenient means of purifying the protein. A variety of peptidases (e.g. enterokinase and thrombin) which cleave a polypeptide at specific sites or digest the peptides from the amino or carboxy termini (e.g. diaminopeptidase) of the peptide chain are known. Furthermore, particular chemicals (e.g. cyanogen bromide) will cleave a polypeptide chain at specific sites. The skilled artisan will appreciate the modifications necessary to the amino acid sequence (and synthetic or semi-synthetic coding sequence if recombinant means are employed) to incorporate site-specific internal cleavage sites. See e.g., P. Carter, "Site Specific Proteolysis of Fusion Proteins", Chapter 13, in *Protein Purification: From Molecular Mechanisms to Large Scale Processes,* American Chemical Society, Washington, D.C. (1990).

In addition to prokaryotes, mammalian host cells and eucaryotic microbes such as yeast may also be used. The simple eucaryote *Saccharomyces cerevisiae,* is the most commonly used eucaryotic microorganism, although a number of other yeasts such as *Kluyveromyces lactis* are also suitable. For expression in Saccharomyces, the plasmid YRp7 (ATCC-40053), for example, may be used. See, e.g., L. Stinchcomb, et al., Nature, 282:39 (1979); J. Kingsman et al., Gene, 7:141 (1979); S. Tschemper et al., Gene, 10:157 (1980). Plasmid YRp7 contains the TRP1 gene which provides a selectable marker for use in a trp1 auxotrophic mutant.

Purification of Recombinantly-Produced MurD Protein

An expression vector carrying the cloned murD gene of *Streptococcus pneumoniae* is transformed or transfected into a suitable host cell using standard methods. Cells which contain the vector are then propagated under conditions suitable for expression of the MurD protein. If the gene is under the control of an inducible promoter then synthetic growth conditions would incorporate the appropriate inducer. The recombinantly produced protein may be purified from cellular extracts of transformed cells by any suitable means. In a preferred process for protein purification the murD gene is modified at the 5' end to incorporate several histidine residues at the amino terminus of the MurD protein product. This "histidine tag" enables a single-step protein purification method referred to as "immobilized metal ion affinity chromatography" (IMAC), essentially as described in U.S. Pat. No. 4,569,794 which hereby is incorporated by reference. The IMAC method enables rapid isolation of substantially pure protein.

Other embodiments of the present invention comprise isolated nucleic acid sequences which encode SEQ ID NO:2. As skilled artisans will recognize, the amino acid compounds of the invention can be encoded by a multitude of different nucleic acid sequences because most of the amino acids are encoded by more than one nucleic acid triplet due to the degeneracy of the amino acid code. Because these alternative nucleic acid sequences would encode the same amino acid sequences, the present invention further comprises these alternate nucleic acid sequences.

The murD gene, which comprises nucleic acid encoding SEQ ID NO:2, may be produced using synthetic methodology. The synthesis of nucleic acids is well known in the art. See, e.g., E. L. Brown, R. Belagaje, M. J. Ryan, and H. G. Khorana, *Methods in Enzymology,* 68:109–151 (1979). The DNA segments corresponding to the murD gene could be generated using a conventional DNA synthesizing apparatus, such as the Applied Biosystems Model 380A or 380B DNA synthesizers (Applied Biosystems, Inc., 850 Lincoln Center Drive, Foster City, Calif. 94404) which employ phosphoramidite chemistry. Alternatively, phosphotriester chemistry may be employed to synthesize the nucleic acids of this invention. [See, e.g., M. J. Gait, ed., *Oligonucleotide Synthesis, A Practical Approach,* (1984).]

In an alternative methodology, murD DNA sequences comprising a portion or all of SEQ ID NO:1 can be generated from *Streptococcus pneumoniae* genomic DNA using suitable oligonucleotide primers complementary to SEQ ID NO:1 or region therein, utilizing the polymerase chain reaction as described in U.S. Pat. No. 4,889,818, which is incorporated herein by reference. Protocols for performing the PCR are disclosed in, *PCR Protocols: A Guide to Method and Applications,* Ed. Michael A. Innis et al., Academic Press, Inc. (1990), which hereby is incorporated by reference.

The ribonucleic acids of the present invention may be prepared using the polynucleotide synthetic methods discussed supra, or they may be prepared enzymatically using RNA polymerases to transcribe a DNA template.

The most preferred systems for preparing the ribonucleic acids of the present invention employ the RNA polymerase from the bacteriophage T7 or the bacteriophage SP6. Both of these RNA polymerases are highly specific and require the insertion of bacteriophage-specific sequences at the 5' end of the template to be transcribed. See, J. Sambrook, et al., supra, at 18.82–18.84.

This invention also provides nucleic acids, RNA or DNA, which are complementary to SEQ ID NO:1 or SEQ ID NO:3.

The present invention also provides probes and primers useful for molecular biology techniques. A compound which encodes for SEQ ID NO:1, SEQ ID NO:3 or a complementary sequence of SEQ ID NO:1 or SEQ ID NO:3, or a fragment thereof, and which is at least 18 base pairs in length, and which will selectively hybridize to *Streptococcus pneumoniae* DNA or mRNA encoding murD, is provided. Preferably, the 18 or more base pair compound is DNA.

These probes and primers can be prepared enzymatically as will be well known to those skilled in the art (See e.g. Sambrook et al. supra). In a most preferred embodiment these probes and primers are synthesized using chemical means as described above.

Another aspect of the present invention is recombinant DNA cloning vectors and expression vectors comprising the nucleic acids of the present invention. Many of the vectors encompassed within this invention are described above. The preferred nucleic acid vectors are those which comprise DNA. The most preferred recombinant DNA vectors comprise the isolated DNA sequence SEQ ID NO:1. Plasmid pPSR10 is an especially preferred DNA vector of the present invention.

The skilled artisan understands that choosing the most appropriate cloning vector or expression vector depends upon a number of factors including the availability of appropriate restriction enzyme sites, the type of host cell into which the vector is to be transfected or transformed, the purpose of the transfection or transformation (e.g., stable transformation as an extrachromosomal element, or integration into the host chromosome), the presence or absence of readily assayable or selectable markers (e.g., antibiotic resistance markers, metabolic markers, or the like), and the number of copies of the gene to be present in the host cell.

Vectors suitable to carry the nucleic acids of the present invention comprise RNA viruses, DNA viruses, lytic bacteriophages, lysogenic bacteriophages, stable bacteriophages, plasmids, viroids, and the like. The most preferred vectors are plasmids.

When preparing an expression vector the skilled artisan understands that there are many variables to be considered, for example, whether to use a constitutive or inducible promoter. Inducible promoters are preferred because they may be the basis for high level, regulatable expression of an operably linked gene. The skilled artisan will recognize a number of inducible promoters and inducers, for example, carbon source, metal ions, heat, and others. The practitioner also understands that the amount of nucleic acid or protein to be produced dictates, in part, the selection of the expression system. The addition of certain nucleotide sequences, such as a sequence encoding a signal peptide preceding the coding sequence, is useful to direct localization of the resulting polypeptide.

Host cells harboring the nucleic acids disclosed herein are also provided by the present invention. A preferred host is *E. coli* which has been transfected or transformed with a vector which comprises a nucleic acid of the present invention.

The present invention also provides a method for constructing a recombinant host cell capable of expressing SEQ ID NO:2, said method comprising transforming a host cell with a recombinant DNA vector that comprises an isolated DNA sequence which encodes SEQ ID NO:2. The preferred host cell is any strain of *E. coli* which can accomodate high level expression of a gene(s) introduced by transformation or transfection. Preferred vectors for expression are those which comprise SEQ ID NO:1. An especially preferred expression vector for use in *E. coli* is plasmid pPSJ318, which comprises SEQ ID NO:1. (See FIGURE). Transformed host cells may be cultured under conditions well known to skilled artisans such that SEQ ID NO:2 is expressed, thereby producing MurD protein in the recombinant host cell.

For the purpose of identifying or developing inhibitors of the stem peptide pathway, it would be desirable to determine those agents which inhibit the MurD step. A method for determining whether a substance will inhibit the enzymatic reaction catalyzed by the MurD protein comprises contacting the MurD protein with a test substance and monitoring MurD enzyme activity by any suitable means.

The instant invention provides such a screening system useful for discovering agents which inhibit the MurD protein product, said screening system comprising the steps of:

a) preparing MurD enzyme;

b) exposing said MurD enzyme to a test inhibitor;

c) introducing substrate; and d) quantifying the loss of activity of said MurD enzyme.

Utilization of the screening system described above provides a means to determine compounds which interfere with stem peptide biosynthesis. This screening system may be adapted to automated procedures such as a PANDEX® (Baxter-Dade Diagnostics) system allowing for efficient high-volume screening of potential therapeutic agents.

In such a screening protocol MurD enzyme is prepared as described herein, preferably using recombinant DNA technology. A sample of a test compound is then introduced into the reaction vessel containing the MurD enzyme, followed by the addition of enzyme substrate. In the alternative, the substrate may be added simultaneously with the test compound. For example, in a preferred method of the invention, radioactively or chemically-labeled substrate may be used. The products of the enzymatic reaction are then quantitated for the chemical label or radioactivity. The absence or diminution of the chemical label or radioactivity indicates the degree to which the reaction is inhibited.

Skilled artisans will recognize that $IC_{50}$ values are dependent on the selectivity of the compound tested. For example, a compound with an $IC_{50}$ which is less than 10 nM is generally considered an excellent candidate for drug therapy. However, a compound which has a lower affinity, but is selective for a particular target, may be an even better candidate. The skilled artisan will recognize that any information regarding inhibitory activity or selectivity of a particular compound is beneficial in the pharmaceutical development of drugs.

The nucleic acid compounds of the present invention may also be used to hybridize to genomic DNA which has been digested with one or more restriction enzymes and run on an electrophoretic gel. The hybridization of radiolabeled probes onto such restricted DNA, usually fixed to a membrane after electrophoresis, is well known in the art. (See, e.g., J. Sambrook, supra.)

The following examples more fully describe the present invention. Those skilled in the art will recognize that the particular reagents, equipment, and procedures described are merely illustrative and are not intended to limit the present invention in any manner.

EXAMPLE 1

Construction of DNA Vector for Expressing
Streptococcus pnuemoniae murD Gene in
Homologous or Heterologous Host Plasmid pPSJ318 (See FIGURE) is an approximately 7500 base pair expression vector suitable for expressing the murD gene of *S. pneumoniae* in the procaryotic host *E. coli*. This plasmid contains an origin of replication (Ori), an ampicillin resistance gene (Amp) useful for selecting cells which have incorporated the vector following a tranformation procedure, and further comprises the lacI gene for repression of the lac operon, as well as the T7 promoter and T7 terminator sequences in operable linkage to the coding region of the murD gene. Parent plasmid pET11A (obtained from Novogen, Madison, Wis.) was linearized by digestion with endonucleases NdeI and BamHI. Linearized pET11A was ligated to a DNA fragment bearing NdeI and BamHI sticky ends and comprising the coding region of the *S. pneumoniae* murD gene.

The murD gene ligated into pPSJ318 was modified at the 5' end (amino terminus of encoded protein) in order to simplify purification of the encoded MurD protein product. For this purpose, an oligonucleotide encoding 8 histidine residues and a factor Xa cleavage site was inserted after the ATG start codon at nucleotide positions 1 to 3 of SEQ ID NO: 1. Placement of the histidine residues at the amino terminus of the encoded protein does not affect its activity and serves only to enable the IMAC one-step protein purification procedure (See below).

EXAMPLE 2

Expression of *Streptococcus pneumoniae* murD
Gene in *Echerichia coli* and Purification of MurD
Enzyme Plasmid pPSJ318 was transformed into *E. coli* BL21 (DE3) (hsdS gal λcIts857 ind1Sam7nin5lacUV5-T7gene 1) using standard methods (See e.g. Sambrook et al. Supra). Transformants, selected for resistance to ampicillin, were chosen at random and tested for the presence of pPSR? by agarose gel electrophoresis using quick plasmid preparations. Id. Colonies identified as containing pPSJ318 were grown, processed, and the protein product encoded by the murD gene was purified by immobilized metal ion affinity chromatography (IMAC), essentially as described in U.S. Pat. No. 4,569,794, the entire contents of which is hereby incorporated by reference.

Briefly, the IMAC column was prepared as follows. A metal-free chelating resin (e.g. SEPHAROSE 6B IDA, Pharmacia) was washed in distilled water to remove preservative substances and infused with a suitable metal ion [e.g. Ni(II), Co(II), or Cu(II)] by adding a 50 mM metal chloride or metal sulfate aqueous solution until about 75% of the interstitial spaces of the resin were saturated with colored metal ion. The column was then ready to receive a crude cellular extract containing the MurD protein product encoded by pPSR10.

After removing unbound proteins and other materials by washing the column with suitable buffer, pH 7.5, the bound protein was eluted in buffer at pH 4.3 essentially as described in U.S. Pat. No. 4,569,794.

EXAMPLE 3

Biochemical Assay for Inhibitors of *Streptococcus pneumoniae* MurD Enzyme Product The activity of the MurD enzyme was assayed by monitoring the appearance of the enzyme product, UDP-MurNAc-L-Ala-D-isoGlu, using high-pressure liquid chromatography detection (HPLC). The enzyme reaction consisted of 0.1M Tris/HCl pH 8.6, 20 mM $MgCl_2$, 5 mM ATP, 100 μM UDP-MurNAc-L-Ala, 50 μM D-glutamic acid, and enzyme in a final volume of 50 μl. Substrate UDP-MurNAc-L-Ala was purified as described in B. Flouret et al., *Reverse-phase high-pressure liquid chromatography of uridine diphosphate N-Acetylmuramyl pentide precursors of bacterial cell wall peptidoglycan,* Anal. Biochem. 114, 59–63 (1981). The mixture was incubated for 30 min. at 37° C., and the reaction terminated with the addition of 10 μl of glacial acetic acid. The amount of product generated was determined by HPLC, essentially as described in Flouret et.al. (Id.). Briefly, the nucleotide precursors were extracted in the cold by trichloroacetic acid and purified by gel filtration on fine SEPHADEX G-25. The UDP-MurNac derivatives were eluted with water in a volume slightly larger than the exclusion volume of the column. Separation and further purification of UDP-MurNAc derivatives were carried out by ion-exchange chromatography on Dowex AG1×2 (200–400 mesh) according to the method of Park & Chatterjee, *Methods in Enzymology,* 8, 466–472 (Academic Press, N.Y. 1966). HPLC analyses were performed with a Waters Associates apparatus consisting of two Model 6000 A solvent delivering systems, a Model 660 solvent programmer, and a Model 450 variable wavelength detector which monitored the eluant at 220 nm or at 262 nm. Peaks were recorded and integrated with a Spectra Physics SP 4100 model computing integrator (Spectra Physics, Santa Clara, Calif.).

Inhibition studies are carried out using the same reaction conditions described in the preceding paragraph. Compounds to be studied for inhibitory activity are added to final concentrations of between 1 mM and 10 mM.

We claim:
1. An isolated nucleic acid compound comprising a sequence encoding the protein described by SEQ ID NO: 2 or enzymatically active fragment thereof wherein said compound has a sequence selected from the group consisting of:

(a)

| | | | |
|---|---|---|---|
| ATGAAAGTAA | TAGATCAATT | TAAAAATAAG | |
| AAAGTTCTTG | TTTTAGGTTT | GGCCAAGTCT | 60 |
| GGTGAATCTG | CAGCTCGTTT | GTTGGACAAG | |
| CTAGGTGCCA | TTGTGACAGT | AAATGATGGG | 120 |
| AAACCTTTCG | AGGACAATCC | AGCTGCCCAA | |
| AGTTTGCTGG | AAGAAGGGAT | CAAGGTCATT | 180 |
| ACAGGTGGCC | ATCCTTTGGA | ACTCTTGGAT | |
| GAAGAGTTTG | CCCTTATGGT | GAAAAATCCA | 240 |
| GGTATCCCCT | ACAACAATCC | CATGATTGAA | |
| AAGGCTTTGG | CCAAGAGAAT | TCCAGTCTTG | 300 |
| ACTGAGGTGG | AATTGGCTTA | TTTGATTTCA | |
| GAAGCACCGA | TTATTGGTAT | CACAGGATCG | 360 |
| AACGGTAAGA | CAACCACAAC | GACTATGATT | |
| GGGGAAGTTT | TGACTGCTGC | TGGGCAACAT | 420 |
| GGTCTTTTAT | CAGGGAATAT | CGGCTATCCT | |
| GCCAGTCAGG | TTGCTCAAAT | AGCATCAGAT | 480 |
| AAGGACACGC | TTGTTATGGA | ACTTTCTTCT | |
| TTCCAACTCA | TGGGTGTTCA | AGAATTCCAT | 540 |
| CCAGAGATTG | CGGTTATTAC | CAACCTCATG | |
| CCAACTCATA | TCGACTACCA | TGGGTCATTT | 600 |
| TCTGAATATG | TAGCAGCCAA | GTGGAATATC | |
| CAGAACAAGA | TGACAGCAGC | TGATTTCCTT | 660 |
| GTCTTGAACT | TTAATCAAGA | CTTGGCAAAA | |
| GACTTGACTT | CCAAGACAGA | AGCCACTGTT | 720 |
| GTACCATTTT | CAACACTTGA | AAAGGTTGAT | |
| GGAGCTTATC | TGGAAGATGG | TCAACTCTAC | 780 |
| TTCCGTGGTG | AAGTAGTCAT | GGCAGCGAAT | |
| GAAATCGGTG | TTCCAGGTAG | CCACAATGTG | 840 |
| GAAAATGCCC | TTGCGACTAT | TGCTGTAGCC | |
| AAGCTTCGTG | ATGTGGACAA | TCAAACCATC | 900 |
| AAGGAAACTC | TTTCAGCCTT | CGGTGGTGTC | |
| AAACACCGTC | TCCAGTTTGT | GGATGACATC | 960 |
| AAGGGTGTTA | AATTCTATAA | CGACAGTAAA | |
| TCAACTAATA | TCTTGGCTAC | TCAAAAAGCC | 1020 |
| TTATCAGGAT | TTGACAACAG | CAAGGTCGTC | |
| TTGATTGCAG | GTGGTTTGGA | CCGTGGCAAT | 1080 |
| GAGTTTGACG | AATTGGTGCC | AGACATTACT | |
| GGACTCAAGA | AGATGGTCAT | CCTGGGTCAA | 1140 |
| TCTGCAGAAC | GTGTCAAACG | GGCAGCAGAC | |
| AAGGCTGGTG | TCGCTTATGT | GGAGGCGACA | 1200 |
| GATATTGCAG | ATGCGACCCG | CAAGGCCTAT | |
| GAGCTTGCGA | CTCAAGGAGA | TGTGGTTCTT | 1260 |
| CTTAGTCCTG | CCAATGCCAG | CTGGGATATG | |
| TATGCTAACT | TTGAAGTACG | TGGCGACCTC | 1320 |
| TTTATCGACA | CAGTAGCGGA | GTTAAAAGAA | 1350 | which is SEQ ID NO:1;

(b)

| | | | |
|---|---|---|---|
| AUGAAAGUAA | UAGAUCAAUU | UAAAAAUAAG | |
| AAAGUUCUUG | UUUUAGGUUU | GGCCAAGUGU | 60 |
| GGUGAAUCUG | CAGCUCGUUU | GUUGGACAAG | |
| CUAGGUGCCA | UUGUGACAGU | AAAUGAUGGG | 120 |
| AAACCUUUCG | AGGACAAUCC | AGCUGCCCAA | |
| AGUUUGCUGG | AAGAAGGGAU | CAAGGUCAUU | 180 |
| ACAGGUGGCC | AUCCUUUGGA | ACUCUUGGAU | |
| GAAGAGUUUG | CCCUUAUGGU | GAAAAAUCCA | 240 |

```
       GGUAUCCCCU    ACAACAAUCC    CAUGAUUGAA                    UUAUCAGGAU    UUGACAACAG    CAAGGUCGUC

AAGGCUUUGG    CCAAGAGAAU    UCCAGUCUUG    300              UUGAUUGCAG    GUGGUUUGGA    CCGUGGCAAU         1080

ACUGAGGUGG    AAUUGGCUUA    UUUGAUUUCA                    GAGUUUGACG    AAUUGGUGCC    AGACAUUACU

GAAGCACCGA    UUAUUGGUAU    CACAGGAUCG    360              GGACUCAAGA    AGAUGGUCAU    CCUGGGUCAA        1140

AACGGUAAGA    CAACCACAAC    GACUAUGAUU                   UCUGCAGAAC    GUGUCAAACG    GGCAGCAGAC

GGGGAAGUUU    UGACUGCUGC    UGGGCAACAU    420              AAGGCUGGUG    UCGCUUAUGU    GGAGGCGACA         1200

GGUCUUUUAU    CAGGGAAUAU    CGGCUAUCCU                   GAUAUUGCAG    AUGCGACCCG    CAAGGCCUAU

GCCAGUCAGG    UUGCUCAAAU    AGCAUCAGAU    480              GAGCUUGCGA    CUCAAGGAGA    UGUGGUUCUU         1260

AAGGACACGC    UUGUUAUGGA    ACUUUCUUCU                   CUUAGUCCUG    CCAAUGCCAG    CUGGGAUAUG

UUCCAACUCA    UGGGUGUUCA    AGAAUUCCAU    540              UAUGCUAACU    UUGAAGUACG    UGGCGACCUC        1320

CCAGAGAUUG    CGGUUAUUAC    CAACCUCAUG                   UUUAUCGACA    CAGUAGCGGA    GUUAAAAGAA        1350

CCAACUCAUA    UCGACUACCA    UGGGUCAUUU    600     which is SEQ ID NO:3;
```

(c) a nucleic acid compound complementary to (a) or (b); and (d) an isolated nucleic acid which hybridizes under selective hybridization conditions to the nucleic acid described by SEQ ID NO: 1, or a nucleic acid which encodes an enzymatically active fragment of the protein described by SEQ ID NO: 2.

2. An isolated nucleic acid compound of claim 1 wherein the sequence of said compound is SEQ ID NO:1 or a sequence complementary to SEQ ID NO:1.

3. An isolated nucleic acid compound of claim 1 wherein the sequence of said compound is SEQ ID NO:3 or a sequence complementary to SEQ ID NO:3.

4. A vector comprising an isolated nucleic acid compound of claim 1.

5. A vector, as in claim 4, wherein said isolated nucleic acid compound is DNA operably linked to a promoter sequence.

6. A host cell containing the vector of claim 4.

7. A host cell containing the vector of claim 5.

8. A method for constructing a recombinant host cell which expresses the protein described by SEQ ID NO:2, said method comprising introducing into said host cell by any suitable means a vector of claim 5.

9. A method for expressing SEQ ID NO:2 in the recombinant host cell of claim 8, said method comprising culturing said recombinant host cell under conditions suitable for gene expression.

* * * * *